US009156750B2

(12) United States Patent (10) Patent No.: US 9,156,750 B2
Eeckhout et al. (45) Date of Patent: Oct. 13, 2015

(54) PURIFICATION OF A HYDROCARBON STREAM (71) Applicant: TOTAL RESEARCH & TECHNOLOGY FELUY, Seneffe (BE)

(72) Inventors: Karel Eeckhout, Leuven (BE); Marc Richet, Mons (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 0 days.

(21) Appl. No.: 14/374,645

(22) PCT Filed: Jan. 24, 2013

(86) PCT No.: PCT/EP2013/051363
§ 371 (c)(1),
(2) Date: Jul. 25, 2014

(87) PCT Pub. No.: WO2013/110719
PCT Pub. Date: Aug. 1, 2013

(65) Prior Publication Data
US 2014/0336346 A1 Nov. 13, 2014

(30) Foreign Application Priority Data

Jan. 26, 2012 (EP) .................................... 12152651

(51) Int. Cl.
C07C 7/148 (2006.01)
C08F 6/02 (2006.01)
C08F 110/06 (2006.01)
C10G 21/16 (2006.01)
C10G 21/20 (2006.01)
C10G 21/27 (2006.01)
C10G 29/20 (2006.01)
C10G 29/22 (2006.01)
C10G 50/00 (2006.01)
C10G 57/02 (2006.01)

(52) U.S. Cl.
CPC ............... *C07C 7/14875* (2013.01); *C08F 6/02* (2013.01); *C08F 110/06* (2013.01); *C10G 21/16* (2013.01); *C10G 21/20* (2013.01); *C10G 21/27* (2013.01); *C10G 29/20* (2013.01); *C10G 29/22* (2013.01); *C10G 50/00* (2013.01); *C10G 57/02* (2013.01); *C10G 2300/201* (2013.01); *C10G 2400/20* (2013.01)

(58) Field of Classification Search
CPC C07C 7/14875; C07C 7/14891; C07C 11/06; C07C 21/16; C08F 6/02; C10G 21/22; C10G 21/24; C10G 21/27; C10G 57/02; C10G 2300/205
USPC ............. 526/72; 585/856, 860, 864, 865, 866
See application file for complete search history.

(56) References Cited

U.S. PATENT DOCUMENTS 3,271,380 A 9/1966 Dietz
2007/0244273 A1* 10/2007 Blackmon et al. .............. 526/82

FOREIGN PATENT DOCUMENTS

| FR | 2581987 A2 | 11/1986 |
| GB | 837088 A | 6/1960 |
| GB | 2007680 A | 5/1979 |
| WO | 2009157770 A1 | 12/2009 |

OTHER PUBLICATIONS

International Search Report issued in PCT/EP2013/051363 dated Sep. 30, 2013 (3 pages).

* cited by examiner

*Primary Examiner* — Fred M Teskin (57) ABSTRACT

A process for producing a purified hydrocarbon stream can include contacting a hydrocarbon stream contaminated with one or more organoaluminum compounds with a chemical agent that is capable of reacting with the one or more organoaluminum compounds.

18 Claims, 3 Drawing Sheets

PURIFICATION OF A HYDROCARBON STREAM

FIELD OF THE INVENTION

The present invention relates to a process for producing a purified hydrocarbon stream by contacting a hydrocarbon stream, which is contaminated with one or more organoaluminum compounds, with a specifically selected chemical agent capable of reacting with said one or more organoaluminum compounds.

The Technical Problem and the Prior Art

Organoaluminum compounds started entering industrial use only in the second part of the $20^{th}$ century. This was primarily due to the fact that they are relatively difficult to produce and highly reactive, thus posing difficulties with respect to their handling in an industrial environment. Today, however, they are routinely used in a number of chemical processes, of which polymerization processes, especially the polymerization of olefins, are the most important ones.

The polymerization of olefins may be done in a polymerization zone generally under elevated temperatures and pressures using for example Ziegler-Natta polymerization catalysts or metallocene-based polymerization catalysts. Ziegler-Natta polymerization catalysts generally comprise a titanium halide on a magnesium halide support. As such they are inactive and require a co-catalyst so as to be able to polymerize. The most widely used co-catalysts are organoaluminum compounds. Metallocene-based polymerization catalysts generally comprise a metallocene on a support, for example a silica. In order to polymerization they must also be activated, which is frequently done with alkylalumoxanes, of which methylalumoxane (MAO) is the most widely used.

Polymerization processes include slurry processes, wherein the polymerization is performed in an inert diluent, and bulk processes, wherein the polymerization is performed in the olefin itself. An example of a slurry process is the polymerization or copolymerization of ethylene or propylene in one or more inert hydrocarbon diluents. An example of the bulk polymerization is the polymerization of propylene.

Following polymerization the polymers are withdrawn from the polymerization zone in form of an effluent, which comprises polymer, olefin, one or more organoaluminum compounds and the optional one or more diluents. Olefin and diluent(s) are separated from the polymer by flashing, e.g. by reducing the pressure, and withdrawing olefin and diluent in gaseous form. Unfortunately, the withdrawn olefin and diluent are in general not pure and may contain contaminants, such as for example the already mentioned organoaluminum compounds.

The presence of such contaminants, particularly the presence of the highly reactive organoaluminum compounds, severely limits the potential further use of the recovered olefin or diluent or both due to problems such as alumina precipitation, corrosion and others. Additionally, the presence of organoaluminum compounds can also be detrimental to and limit the use of downstream equipment, such as for example a membrane separation unit. In the case of propane, examples of potential further use include use as fuel gas, co-cracking gas or as liquefied petroleum gas (LPG).

Organoaluminum compounds may be eliminated from the product stream by injecting for example water or alcohols or other compounds known to irreversibly react with the organoaluminum compounds and thus to deactivate them. In case of water injection, consecutive precipitation of alumina and filtration to remove the alumina from the hydrocarbon stream are required. However, filtration of alumina is very difficult, and the injection of small water quantities into such a stream leads to frequent blockage at the injection point. In consequence, such a system is difficult to operate and requires high maintenance.

The problems associated with the presence of organoaluminum compounds in the off-gas of a chemical process can be circumvented for example by burning the off-gas in a flare. However, in view of the depletion of natural resources and the reduction of emissions, such simple disposal is no longer a readily accepted alternative.

It is therefore an object of the present invention to overcome these drawbacks and to provide a process for the purification of a contaminated hydrocarbon stream comprising one or more organoaluminum compounds.

Additionally, it is an object of the present invention to provide a process for the at least partial elimination of one or more organoaluminum compounds from a hydrocarbon stream.

In other words, it is an object of the present invention to provide a process for the purification of a hydrocarbon stream comprising one or more organoaluminum compounds such that the content of aluminum in the resulting purified hydrocarbon stream is lower than in the contaminated hydrocarbon stream, i.e. the hydrocarbon stream before the purification.

It is a particular object of the present invention to provide a process for the purification of a hydrocarbon stream comprising propane.

It is a preferred object of the present invention to provide a process for the purification of a hydrocarbon stream comprising one or more organoaluminum compounds such that the purified hydrocarbon stream has a content of aluminum adapted to the further use of the purified hydrocarbon stream, for example of at most 10 ppm or 5 ppm or 4 ppm or 3 ppm or 2 ppm or 1 ppm.

BRIEF DESCRIPTION OF THE INVENTION

The present inventors have found that the above objects can be attained either individually or in any combination by contacting a contaminated hydrocarbon stream comprising one or more organoaluminum compounds with a specifically selected chemical agent.

Hence, the present application discloses a process for producing a purified hydrocarbon stream, said process comprising the steps of (i) contacting in a contact vessel a contaminated hydrocarbon stream and a chemical agent, wherein the contaminated hydrocarbon stream comprises one or more organoaluminum compounds and the chemical agent is capable of reacting with said one of more organoaluminum compounds, thereby producing a purified hydrocarbon stream; and (ii) withdrawing said purified hydrocarbon stream from said contact vessel.

Further, the present application discloses a chemical manufacturing plant comprising a contact vessel, wherein a contaminated hydrocarbon stream is contacted with a chemical agent, wherein the contaminated hydrocarbon stream comprises one or more organoaluminum compounds and the chemical agent is capable of reacting with said one of more organoaluminum compounds.

DETAILED DESCRIPTION OF THE INVENTION

The term "hydrocarbon" is used to denote a chemical compound that consists of hydrogen atoms and carbon atoms only.

The term "hydrocarbon stream" as used herein denotes a stream comprising one or more hydrocarbons as defined below. The hydrocarbon stream comprises preferably at least 90 wt %, more preferably at least 95%, even more preferably at least 97 wt % and most preferably at least 99 wt %, relative to the total weight of said hydrocarbon stream, of the one or more hydrocarbons.

Preferably the hydrocarbons used herein have a molecular weight of at most 250 g/mol, more preferably of at most 200 g/mol and most preferably of at most 150 g/mol. Preferably the hydrocarbons used herein have a molecular weight of at least 10 g/mol and most preferably of at least 20 g/mol.

Preferably the hydrocarbon stream comprises at least one of the group consisting of olefins, alkanes, and aromatic hydrocarbons. Most preferably, the hydrocarbon stream comprises at least an olefin or an alkane.

Preferred olefins are olefins having from one to ten carbon atoms. More preferred olefins are selected from the group consisting of ethylene, propylene, 1-butene, 2-butene, 1-pentene, 2-pentene, 1-hexene, 2-hexene, 3-hexene, 1-heptene, 2-heptene, 3-heptene, 1-octene, 2-octene, 3-octene, nonene, decene, and 1,3-butadiene. Even more preferred olefins are selected from the group consisting of ethylene, propylene, 1-butene, 1-hexene and 1-octene. Still even more preferred olefins are ethylene and propylene. The most preferred olefin is propylene.

Preferred alkanes are alkanes having from one to ten carbon atoms. More preferred alkanes are selected from the group consisting of methane, ethane, propane, butane, iso-butane, pentane, hexane, heptane and octane. Even more preferred alkanes are those having from one to four carbon atoms. Still even more preferred alkanes are ethane, propane, n-butane and iso-butane. The most preferred alkanes are propane and iso-butane.

Preferred aromatic hydrocarbons are selected from the group consisting of benzene, toluene, xylene (ortho-, meta- and para-xylene) and styrene.

The present hydrocarbon stream may also comprise a blend of for example an olefin as defined above and an alkane as defined above. A non-limiting example of a mixture of an olefin and alkane is a mixture of propylene and propane, or a mixture of ethylene and ethane, or a mixture of ethylene and iso-butane, or a mixture of ethylene, hexene and iso-butane, or a mixture of ethylene, butene and iso-butane.

The term "reacting" is used in a general way and may for example denote the formation of covalent chemical bonds as well as the formation of coordinative bonds.

The terms "purification" or "purifying" or "purify" are used to denote the at least partial removal of organoaluminum compound(s) from a contaminated hydrocarbon stream comprising one of more organoaluminum compounds.

Throughout this application the aluminum content is indicated in ppm Al relative to the total weight of the hydrocarbon stream. It is noted that "aluminum content" refers to the respective weight of aluminum only, not to the respective total weight of organoaluminum compound(s).

In a general form the present process for producing a purified hydrocarbon stream comprises the steps of (i) contacting in a contact vessel a contaminated hydrocarbon stream and a chemical agent, thereby producing a purified hydrocarbon stream, and (ii) withdrawing said purified hydrocarbon stream from said contact vessel. Said contaminated hydrocarbon stream comprises one or more organoaluminum compounds. The term "chemical agent" as used herein may also be read in the sense of "at least one chemical agent", though a single chemical agent is preferred. The term "contaminated hydrocarbon stream" is used to denote a hydrocarbon stream comprising one or more organoaluminum compounds before being contacted in the contact vessel with the chemical agent. The term "purified hydrocarbon stream" is used to denote a hydrocarbon stream after having been contacted with the chemical agent.

Preferably, said one or more organoaluminum compounds comprised in the contaminated hydrocarbon stream are selected from the group consisting of organoaluminum compounds represented by the general formula $R_{3-n}AlX_n$ (I), wherein each R is independently selected from alkyl having from one to ten carbon atoms, each X is independently a halogen atom, and n is 0, 1 or 2; alkylalumoxanes wherein alkyl is selected from alkyl having from one to ten carbon atoms; and blends of both.

Examples of alkyl groups having from one to ten carbon atoms are methyl, ethyl, n-propyl, iso-propyl, n-butyl, sec-butyl, tert-butyl, pentyl, hexyl, heptyl, octyl, nonyl and decyl.

With regards to the organoaluminum compound(s) of general formula (I), preferably R is an alkyl having from one to six carbons atoms, such as for example methyl, ethyl, n-propyl, iso-propyl, n-butyl, sec-butyl, tert-butyl, pentyl and hexyl. Most preferably R is ethyl.

With regards to the organoaluminum compound(s) of general formula (I), preferably X is selected from the group consisting of fluorine, chlorine, bromine and iodine. Most preferably X is chlorine.

With regards to the organoaluminum compound(s) of general formula (I), preferably n is 0 or 1, and most preferably n is 0.

Exemplary organoaluminum compounds of general formula (I) include trimethylaluminum ($Me_3Al$), triethylaluminum ($Et_3Al$, frequently referred to as "TEAL"), tri-n-propylaluminum ($nPr_3Al$), tri-iso-propylaluminum ($iPr_3Al$), tri-n-butylaluminum ($nBu_3Al$), tri-iso-butylaluminum ($iBu_3Al$, frequently referred to as "TIBAL"), tri-sec-butylaluminum ($secBu_3Al$), and tri-octyl-aluminum. Triethylaluminum is the most preferred one.

Alkylalumoxanes may be produced by hydrolysis of the respective trialkylaluminum. Preferred examples of alkylalumoxanes include methylalumoxane (MAO), ethylalumoxane, n-propylalumoxane, iso-propylalumoxane, n-butylalumoxane, iso-butylalumoxane, sec-butylalumoxane, and octylalumoxane. Methylalumoxane (MAO) is most preferred.

The chemical agent used in the present process needs to be capable of reacting with such organoaluminum compounds. For the purposes of the present application the term "capable of reacting" is used to denote that the equilibrium between reactants, i.e. chemical agent and organoaluminum compound(s), and products lies almost entirely on the product side. Preferably, at least 90 mol % of the initial amount of reactants is present as product, more preferably at least 95 mol %, even more preferably at least 97 mol %, and most preferably at least 99 mol %.

Preferably, said chemical agent comprises at least one compound selected from the list consisting of H—$X^1$, $X^1$-$A^1$-$X^2$, $X^1$-$A^1$-$A^2$-$X^2$ and $X^1$-$A^3$=$A^4$-$X^2$, wherein $A^1$ and $A^2$ are independently selected from the group consisting of $CR^1R^2$, C=O and $NR^1$, of which $CR^1R^2$ and C=O are preferred and $CR^1R^2$ is most preferred;

$A^3$ and $A^4$ are either independently selected from the group consisting of $CR^1$ and N or alternatively both, $A^3$ and $A^4$, are carbon forming part of an aromatic ring or fused ring system; of which is preferred that $A^3$ and $A^4$ are $CR^1$ or $A^3$ and $A^4$ are carbon forming part of an aromatic ring or fused ring system;

$X^1$ and $X^2$ are independently selected from the group consisting of $OR^1$, $SR^1$, =$NR^1$, $NR^1R^2$, $PR^1R^2$, C(=O)$R^1$, C(=O)$OR^1$, OC(=O)$R^1$, C(=O)$NR^1R^2$ and $NR^1$C(=O)$R^2$, of which $OR^1$, =$NR^1$, $NR^1R^2$, C(=O)$OR^1$ and C(=O)$NR^1R^2$ are preferred; and $R^1$ and $R^2$ are independently selected from the group consisting of hydrogen, alkyl, aryl, substituted alkyl and substituted aryl, wherein substituted alkyl denotes an alkyl substituted with $X^1$ and substituted aryl denotes an aryl substituted with $X^1$;

with the provision that H—$X^1$ is not HOH.

Components $A^1$, $A^2$, $A^3$, $A^4$, $X^1$, $X^2$, $R^1$ and $R^2$ may be chosen such that one or more, preferably six-membered, saturated or unsaturated rings may be formed. Optionally, such rings may also be fused. For example, in $X^1$-$A^1$-$X^2$ component $A^1$, and in $X^1$-$A^1$-$A^2$-$X^2$ component $A^1$ or component $A^2$ or both may be a cyclohexyl ring. Or for example, in) $X^1$-$A^1$-$A^2$-$X^2$ with $A^1$ and $A^2$ both being $CR^1R^2$ both substituents $R^1$ together may form —(CH$_2$—)$_4$—, thus resulting in a cyclohexyl ring. Or for example, compound $X^1$-$A^3$=$A^4$-$X^2$ with $A^3$ and $A^4$ forming an ortho-disubstituted benzene ring as shown in formula (II) below. Or for example, in $X^1$-$A^3$=$A^4$-$X^2$ component $X^1$ may be =$NR^1$, components $A^3$ and $A^4$ may be $CR^{1'}$ and $CR^{1''}$, with $R^1$, $R^{1'}$ and $R^{1''}$ chosen such that the resulting compound is a quinoline-derivative, an example of which is shown in formula (III) below.

It is noted that, as is shown in formula (III), =$NR^1$ may also indicate that the nitrogen atom forms part of an aromatic ring or an aromatic fused ring system.

With regards to $R^1$ and $R^2$ in case they are a substituted alkyl: Preferably $R^1$ and $R^2$ are independently selected from the group consisting of (—CH$_2$—CH$_2$—O)$_m$—$R^3$, (—CH$_2$—CH$_2$—S)$_m$—$R^3$, (—CH$_2$—CH$_2$—$NR^3$)$_m$—$R^3$, (—CH$_2$—CH$_2$—$PR^3$)$_m$—$R^3$, (—CH$_2$—C(=O))$_m$—$R^3$, (—CH$_2$—C(=O)O)$_m$—$R^3$, (—CH$_2$—OC(=O))$_m$—$R^3$, (—CH$_2$—C(=O)$NR^3$)$_m$—$R^3$ and (—CH$_2$—$NR^3$C(=O))$_m$—$R^3$, wherein m is a number ranging from 1 to 400, and in one aspect is 1 or 2 or 3, and $R^3$ is selected from the group consisting of hydrogen, aryl and alkyl having from 1 to 40 carbon atoms. With respect to $R^3$, the preferred aryl is phenyl.

With regards to $R^1$ and $R^2$ in case they are a substituted aryl: Preferably $R^1$ and $R^2$ are independently selected from the group consisting of -(-Ph-O)$_m$—$R^3$, (-Ph-S)$_m$—$R^3$, (-Ph-$NR^3$)$_m$—$R^3$, (-Ph-$PR^3$)$_m$—$R^3$, (-Ph-C(=O))$_m$—$R^3$, (-Ph-C(=O)O)$_m$—$R^3$, (-Ph-OC(=O))$_m$—$R^3$, (-Ph-C(=O)$NR^3$)$_m$—$R^3$ and (-Ph-$NR^3$C(=O))$_m$—$R^3$, wherein Ph is a phenylene, m is a number ranging from 1 to 400, and in one aspect is 1 or 2 or 3, and $R^3$ is selected from the group consisting of hydrogen, aryl and alkyl having from 1 to 40 carbon atoms. More preferably $R^1$ and $R^2$ are independently selected from the group consisting of -(-Ph-O)$_m$—$R^3$, (-Ph-$NR^3$)$_m$—$R^3$, (-Ph-C(=O)O)$_m$—$R^3$, (-Ph-OC(=O))$_m$—$R^3$, (-Ph-C(=O)$NR^3$)$_m$—$R^3$ and (-Ph-$NR^3$C(=O))$_m$—$R^3$. With respect to $R^3$, the preferred aryl is phenyl.

With respect to $R^1$ and $R^2$ the most preferred aryl is an ortho-phenylene. Following IUPAC-nomenclature, the term "phenylene" refers to the bivalent radical of benzene, said radical having the general formula C$_6$H$_4$. Ortho-phenylene may be represented by "1,2-C$_6$H$_4$".

More preferably, said chemical agent is selected from the group consisting of $X^1$—$CR^4R^5$—$X^2$, $X^1$—$NR^6$—$X^2$, $X^1$—C(=O)—C(=O)—$X^2$, $X^1$—$CR^4R^5$—$CR^4R^5$—$X^2$ and $X^1$—$CR^7$=$CR^7$—$X^2$, wherein —$X^1$ and $X^2$ are independently selected from the group consisting of $OR^1$, $SR^1$, =$NR^1$, $NR^1R^2$, $PR^1R^2$, C(=O)$R^1$, C(=O)$OR^1$, OC(=O)$R^1$, C(=O)$NR^1R^2$ and $NR^1$C(=O)$R^2$, of which $OR^1$, =$NR^1$, $NR^1R^2$, C(=O)$OR^1$ and C(=O)$NR^1R^2$ are preferred;

$R^1$ and $R^2$ are independently selected from the group consisting of hydrogen, alkyl, aryl, substituted alkyl and substituted aryl, wherein substituted alkyl denotes an alkyl substituted with $X^1$ and substituted aryl denotes an aryl substituted with $X^1$ and preferably are as defined above;

$R^4$ and $R^5$ are independently selected from the group consisting of hydrogen, alkyl, aryl and substituted alkyl, with substituted alkyl as defined above with m being 1 or 2 or 3; any $R^4$ and $R^5$ on the same carbon atom or neighboring carbon atoms may together form a saturated or unsaturated, preferably six-membered, ring, of cyclohexyl is preferred;

$R^6$ is hydrogen, alkyl, aryl and substituted alkyl, with substituted alkyl as defined above with m being 1 or 2 or 3;

$R^7$ is selected from the group consisting of hydrogen, alkyl, aryl and substituted alkyl, with substituted alkyl as defined above with m being 1 or 2 or 3; two groups $R^7$ on neighboring carbon atoms may together form a saturated or unsaturated, preferably six-membered, ring, of which cyclohexenyl and phenylene are preferred.

Even more preferably, said chemical agent is selected from the group consisting of the following classes of compounds (A) HO—CH$_2$—CH$_2$—O—(CH$_2$—CH$_2$—O)$_m$—H, wherein m is from 0 to 400;

(B) ($R^8$OOC—CH$_2$—)$_2$N—CHR$^9$—CHR$^9$—N(—CH$_2$—COOR$^8$)$_2$, wherein $R^8$ is selected from the group consisting of hydrogen, aryl and alkyl having from 1 to 40 carbon atoms, and more preferably $R^8$ is selected from the group consisting of hydrogen, methyl, ethyl, propyl, butyl and tert-butyl; and most preferably $R^8$ is hydrogen; and wherein $R^9$ is either hydrogen or —CH$_2$—CH$_2$—;

(C) a metal salt of (HOOC—CH$_2$—)$_2$N—CHR$^9$—CHR$^9$—N(—CH$_2$—COOH)$_2$, wherein the metal preferably is Na; and wherein $R^9$ is either hydrogen or —CH$_2$—CH$_2$—;

(D) ethoxylated alkylamines of formula $(C_pH_{2p+1})_qN(CH_2—CH_2—OH)_{3-q}$ with p being in the range from 1 to 30, more preferably in the range from 10 to 20; and q being 0, 1 or 2;

(E) $N(CH_2—COOH)_3$, $R^{10}N(CH_2—COOH)_2$, $R^{10}{}_2N(CH_2—COOH)$ and the respective sodium salts, wherein $R^{10}$ is selected from the group consisting of hydrogen, aryl and alkyl having from 1 to 40 carbon atoms; and (F) $X^3-A^5-X^4-(-A^6-X^4)_n—X^5$, wherein $A^5$ and $A^6$ may independently be selected from the group consisting of —$CH_2$—$CH_2$—, —CH═CH— and ortho-phenylene; and wherein $X^3$ and $X^5$ are $OX^6$ or $NX^6X^7$ and $X^4$ is O or $NX^6$, with $X^6$ and $X^7$ being independently selected from the group consisting of —$CH_2$—$COOR^{11}$, —$CH_2$—$CH_2$—$OR^{11}$, —$CH_2$—$CH_2$—$NR^{11}{}_2$ and —$CH_2$—C(═O)$NR^{11}{}_2$, wherein n is in the range from 0 to 400, more preferably n is in the range from 1 to 10, even more preferably n is 0, 1, 2, 3, 4 or 5, and most preferably n is 1 or 2; and wherein $R^{11}$ is selected from the group consisting of hydrogen, aryl and alkyl having from 1 to 40 carbon atoms, with $R^{11}$ being more preferably selected from the group consisting of hydrogen, aryl and alkyl having from one to ten carbon atoms, and with $R^{11}$ being most preferably hydrogen; wherein consecutive units —$CH_2$—$CH_2$—$X^4$ may differ from one another;

(G) beta-diketones and beta-diketone derivatives of formula $R^{12}$—C(═O)—$CR^{13}R^{14}$—C(═O)—$R^{15}$ or of formula $X^6$—C(═O)—$CR^{13}R^{14}$C(═O)—$X^7$ wherein $X^6$ and $X^7$ are independently $OR^{12}$ or $NR^{12}R^{13}$, and wherein $R^{12}$, $R^{13}$, $R^{14}$ and $R^{15}$ are independently selected from the group consisting of hydrogen, aryl and alkyl having from 1 to 40 carbon atoms, preferably are independently selected from the group consisting of hydrogen, aryl and alkyl having from one to ten carbon atoms;

(H) 1,2-dihydroxybenzene; and (J) 8-$X^8$-quinoline, wherein $X^8$ is selected from the group consisting of OH and $NR^{16}{}_2$ with $R^{16}$ selected from the group consisting of hydrogen and methyl with hydrogen being preferred.

Specific examples for (A) include glycol and polyethylene glycol, said polyethylene glycol having a preferred molecular weight of at least 100 and of at most 5000, more preferably of at most 4000 or 3000, even more preferably of at most 2000 and most preferably of at most 1000 g/mol.

Specific examples for (B) and (C) include (HOOC—$CH_2$)$_2$N—$CH_2$—$CH_2$—N($CH_2$—COOH)$_2$(ethylenediaminetetraacetic acid, EDTA, CAS-number 60-00-4), cyclohexanediamine-tetraacetic acid and their respective di-sodium salts.

Specific examples for (D) include the following compounds of general formula $(C_pH_{2p+1})N(CH_2—CH_2—OH)_2$, wherein p is from 12 to 18 (N—($C_{12}$-$C_{18}$ alkyl)bis(2-hydroxyethyl)amine, CAS-number 71786-60-2). Such compounds are commercially available for example as Atmer 163 (CAS-number 107043-84-5) or Armostat 400 (N—($C_{12}$-$C_{14}$ alkyl)bis(2-hydroxyethyl)amine, CAS-number 61791-31-9) or Armostat 300 (N—($C_{14}$-$C_{18}$ alkyl)bis(2-hydroxyethyl)amine, CAS-number 61791-44-4).

Specific examples for (E) include N($CH_2$—COOH)$_3$ (nitrilotriacetic acid, CAS-number 139-13-9) and the respective sodium salts.

Specific examples for (F) include (HOOC—$CH_2$)$_2$N—$CH_2$—$CH_2$—N($CH_2$—COOH)—$CH_2$—$CH_2$—N($CH_2$—COOH)$_2$ (diethylenetriaminepentaacetic acid, DTPA, CAS-number 67-43-6), (HOOC—$CH_2$)$_2$N—($CH_2$—$CH_2$—O)$_2$—$CH_2$—$CH_2$—N($CH_2$—COOH)$_2$ (ethylenebis(oxyethylenenitrilo)tetraacetic acid, EGTA, CAS-number 67-42-5), (HOOC—$CH_2$)$_2$N-(1,2-$C_6H_4$)—O—$CH_2$—$CH_2$—O-(1,2-$C_6H_4$)—N($CH_2$—COOH)$_2$ (2,2'-(ethylenedioxy)dianiline-N,N,N',N'-tetraacetic acid, BAPTA, CAS-number 85233-19-8), [(HOOC—$CH_2$)$_2$N—$CH_2$—$CH_2$—N(—$CH_2$—COOH)—$CH_2$—]$_2$ (triethylenetetraminehexaacetic acid, TTHA, CAS-number 869-52-3), and (HOOC—$CH_2$)$_2$N—$CH_2$—$CH_2$—N($CH_2$—COOH)($CH_2$—$CH_2$—OH) (N-(2-hydroxyethyl)-ethylenediamine-N,N,N'-triacetic acid, HEDTA) and the respective trisodium salt.

Specific examples for (J) include 8-quinolinol and 8-amino-quinoline.

Still even more preferably the chemical agent is selected from class (A) or class (D). Most preferably the chemical agent is selected from class (D).

Preferably, said chemical agent is suspended or dissolved in a liquid, thus forming a suspension or solution, in the following referred to as "solution", wherein said liquid is chemically inert towards organoaluminum compounds. Examples of such chemically inert diluents are saturated hydrocarbons, such as for example mineral oil.

Preferably, the concentration of chemical agent in said liquid is of at least 5 wt % and most preferably of at least 10 wt %, relative to the amount of said liquid. Preferably, said concentration is of at most 90 wt %, more preferably of at most 80 wt %, even more preferably of at most 70 wt %, and most preferably of at most 60 wt %, relative to the amount of said liquid. Alternatively, it is also possible to use the chemical agent in pure form, i.e. without the chemical agent being suspended or dissolved in a liquid. The concentration of chemical agent in said liquid is given as wt % relative to the total weight of the solution.

The contact vessel used in the present process may be any vessel that allows bringing into contact the contaminated hydrocarbon stream and the chemical agent. For example, the contaminated hydrocarbon stream may simply be bubbled through the chemical agent or a solution of such chemical agent. Preferably, said contact vessel is a continuously stirred tank reactor or a gas/liquid contactor of the shower tray type, with the gas/liquid contactor of the shower type being preferred. It is noted that with respect to the type of tray or packing any type is considered suitable.

With regards to the conditions in the contact vessel, it is preferred that the temperature therein is above the boiling point of the contaminated hydrocarbon stream. When feeding it to the contact vessel the contaminated hydrocarbon stream is preferably heated in order to avoid condensation in the contact vessel. Such condensation could lead to an accumulation of liquid in the contact vessel and eventually to the contact vessel becoming inoperable due to the presence of too much liquid. More preferably, the contaminated hydrocarbon stream is superheated when being fed to the contact vessel.

The aluminum content of the contaminated hydrocarbon stream strongly depends upon the chemical process and its respective process conditions, from which the contaminated hydrocarbon stream originates. Hence, the aluminum content of the contaminated hydrocarbon stream can vary within very wide ranges, for example from 1 ppm to 10000 ppm, or for example from 1 ppm to 1000 ppm. A contaminated hydrocarbon stream originating from an olefin polymerization process may for example have an aluminum content of at least 1 ppm and of at most 100 ppm.

The purified hydrocarbon stream is characterized by an aluminum content that is lower than the aluminum content of the contaminated hydrocarbon stream. The purified hydrocarbon stream has an aluminum content preferably of at most 90 wt % or 80 wt % or 70 wt %, more preferably of at most 60 wt % or 50 wt %, even more preferably of at most 40 wt % or 30 wt %, still even more preferably of at most 20 wt % or 10 wt % and most preferably of at most 5 wt % of the aluminum content of the contaminated hydrocarbon stream. For example, if the contaminated hydrocarbon stream comprises 100 ppm of aluminum and the purified hydrocarbon stream 10 ppm, the aluminum content of the purified hydrocarbon stream is 10 wt % of the aluminum content of the contaminated hydrocarbon stream.

The extent of reduction of the aluminum content from contaminated hydrocarbon stream to purified hydrocarbon stream can be controlled for example by the concentration of the solution of chemical agent or by the residence time of the contaminated hydrocarbon stream in the contact vessel. By changing these parameters the aluminum content of the purified hydrocarbon stream can be targeted such that the concentration of organoaluminum compound(s) in the purified hydrocarbon stream is such that the purified hydrocarbon is suited for the intended further use. For example, the aluminum content of the purified hydrocarbon stream is preferably at most 10 ppm, more preferably at most 5 ppm or 4 ppm, even more preferably at most 3 ppm, still even more preferably at most 2 ppm, and most preferably at most 1 ppm.

The aluminum content of a hydrocarbon stream may be determined by coupled plasma technique with atomic emission spectroscopy. A sample of the hydrocarbon stream may for example be directly injected into the flame of the atomic emission spectrometer and analyzed as indicated in the test methods.

From the contact vessel a solution comprising the chemical agent and the reaction product(s) of chemical agent and organoaluminum compound(s) is recovered; said solution is in the following referred to as "recovered solution". Depending upon the type of contact vessel used, said recovery can be done either in a continuous or discontinuous way. In case of discontinuous recovery the solution comprising chemical agent and the reaction product(s) of chemical agent and organoaluminum compound(s) is only removed from the contact vessel once the concentration of organoaluminum compound(s) becomes to high too work safely. In the case of continuous recovery, the solution comprising the chemical agent and the reaction product(s) of chemical agent and organoaluminum compound(s) is continuously removed from the contact vessel and may then either re-introduced directly into the contact vessel or before being re-introduced into the contact vessel pass through an intermediate stage, such as for example a storage stage or a cleansing stage.

In said cleansing stage the reaction product(s) of chemical agents and one or more organoaluminum compounds are removed from the stream. The cleansing stage may either be performed in a continuous manner or in a discontinuous manner. In case of discontinuous cleansing, the reaction product(s) of chemical agent and organoaluminum compound(s) are allowed to accumulate until the concentration of organoaluminum compounds becomes too high to work safely. In case of continuous cleansing, the reaction product(s) of chemical agent and organoaluminum compound(s) are continuously removed from the recovered solution. In any case, it preferred that the concentration of organoaluminum compounds is at most 25 wt %, relative to the total weight of said recovered solution.

If said cleansing is done in a continuous manner, the stream of reaction product of chemical agent and organoaluminum compound(s) withdrawn from the contact vessel is directly discarded and the stream of chemical agent fed to the contact vessel contains only fresh chemical agent. If the chemical agent is for example $C_{12-14}N(CH_2—CH_2—OH)_2$ or $C_{14/16}N(CH_2—CH_2—OH)_2$ it can also be imagined to treat the stream of reaction product of chemical agent and organoaluminum compound(s) with water to produce alumina, thereby setting free the chemical agent, which can then be recycled to the contact vessel.

If said cleansing is done in a discontinuous manner, the reaction product(s) of chemical agent and organoaluminum compound(s) is(are) allowed to accumulate in the system until the concentration of organoaluminum compounds in the recovered solution reaches at most 25 wt %, relative to the total weight of said recovered solution. The totality of the reaction product(s) accumulated is removed and fresh chemical agent is introduced into the system. When working in a discontinuous manner, the amount of unused chemical agent is preferably high enough to allow functioning of the purification process over a longer period, so as to minimize interruptions.

Figure 1:
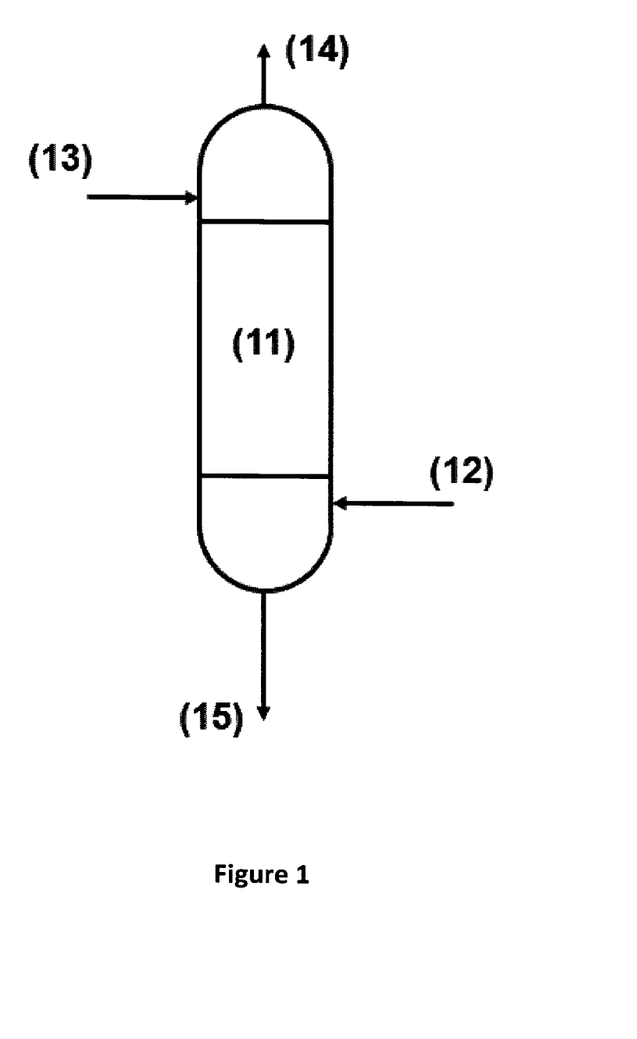
FIG. 1 shows a non-limiting exemplary schematic representation of the present process with the contact vessel being of the shower tray type.

FIG. 1 shows a non-limiting exemplary schematic representation of the present process with the contact vessel being of the shower tray type. A contaminated hydrocarbon stream (12) is fed to the contact vessel (11) near its bottom. A flow (13) of chemical agent is fed near the top to the contact vessel (11) either in pure form or as solution or a dispersion. In the contact vessel (11) the hydrocarbon stream and the flow of chemical agent run countercurrent and are thus brought into contact with one another, allowing the chemical agent and the one or more organoaluminum compounds to react and form the respective reaction product(s), and thereby purifying the hydrocarbon stream. A purified hydrocarbon stream (14) is recovered as overhead at or near the top of the contact vessel (11). A stream (15), which comprises unreacted chemical agent and the reaction product(s) of chemical agent and organoaluminum compound(s), is recovered at or near the bottom of the contact vessel (11).

Preferably, the contaminated hydrocarbon stream originates from a polymerization process. In said polymerization process at least one olefin monomer is polymerized in a polymerization zone in a polymerization medium in presence of a polymerization catalyst. Said olefin monomer may be as defined earlier in this application. Said polymerization medium comprises polymer solids, one or more organoaluminum compounds and at least one olefin monomer, which are withdrawn together as effluent from the polymerization zone. Optionally, the polymerization medium may also comprise other components in minor amounts, such as for example hydrogen. Generally, the polymerization catalyst residues are withdrawn from the polymerization zone as part of the polymer solids.

Hence, a preferred process for producing a purified hydrocarbon stream comprises the steps of
(a) polymerizing at least one olefin monomer in a polymerization zone in a polymerization medium to produce a polymer, said polymerization medium comprising polymer solids, one or more organoaluminum compounds and the at least one olefin monomer;
(b) withdrawing from said polymerization zone an effluent comprising the polymer solids, the one or more organoaluminum compounds and the at least one olefin monomer;
(c) separating from said effluent a contaminated hydrocarbon stream comprising the at least one olefin monomer and the one or more organoaluminum compounds;
(d) feeding at least part of the contaminated hydrocarbon stream of the preceding step to a contact vessel;
(e) contacting in the contact vessel the contaminated hydrocarbon stream and a chemical agent, wherein the contaminated hydrocarbon stream comprises one or more organoaluminum compounds and the chemical agent is capable of reacting with said one or more organoaluminum compounds, thereby producing a purified hydrocarbon stream and a reaction product of said one or more organoaluminum compounds and said chemical agent; and (f) withdrawing said purified hydrocarbon stream from said contact vessel.

In order to reduce the aluminum content in the hydrocarbon stream it is necessary that in step (d) at least part of the contaminated hydrocarbon stream is fed to the contact vessel, wherein the contaminated hydrocarbon stream is subsequently contacted with the chemical agent as defined previously in this application. The part of the contaminated hydrocarbon stream fed to the contact vessel in step (d) may have the same chemical composition as the part not fed to the contact vessel. Alternatively, the two parts may have different chemical compositions. Such difference in chemical composition may for example be obtained by distillation of the contaminated hydrocarbon stream.

The part of the contaminated hydrocarbon stream contacted with the chemical agent is preferably at least 10 wt % or at least 20 wt % or at least 30 wt %, more preferably at least 40 wt % or at least 50 wt %, even more preferably at least 60 wt % or at least 70 wt %, still even more preferably at least 80 wt % or at least 90 wt % with respect to the total weight of the contaminated hydrocarbon stream. Most preferably, the entire contaminated hydrocarbon stream is contacted with the chemical agent.

It is preferred that the polymerization medium in step (a), the effluent in step (b) and the contaminated hydrocarbon stream in step (c) further comprise a diluent. Suitable diluents are hydrocarbons that are inert under polymerization conditions. Hence, preferred diluents are alkanes having from one to ten carbon atoms. Examples of such preferred diluents are methane, ethane, propane, butane, iso-butane, pentane, hexane, heptane and octane. Most preferred diluents are selected from the group consisting of propane, butane, iso-butane, pentane and hexane. It is noted that such diluents may intentionally or unintentionally be added to the polymerization medium. For example, due to the fact that propylene commonly comprises propane, the respective polymerization medium may then by consequence also comprise propane.

If such diluent is present, it is preferred that the present process further comprises a separation step, either following step (c) or following step (f). In such separation step the diluent and the at least one olefin monomer is separated from the contaminated hydrocarbon stream. By "separating" is meant that at least 90 wt % of the amount of the at least one olefin monomer in the contaminated hydrocarbon stream is obtained as a separate stream.

If said separation step follows step (c), the above process further comprises the following step (c') separating the at least one olefin monomer from the contaminated hydrocarbon stream of step (c).

If said separation step follows step (f), the above process further comprises the following step (f') separating the at least one olefin monomer from the purified hydrocarbon stream obtained in step (f).

Preferably, the contaminated hydrocarbon stream originates from a polymerization process, wherein the at least one olefin monomer is as defined above.

More preferably, the contaminated hydrocarbon stream originates from a polymerization process wherein the at least one olefin monomer is ethylene or propylene, and wherein the diluent—if present—is selected from the group consisting of propane, butane, iso-butane, pentane and hexane.

Most preferably, the contaminated hydrocarbon stream originates from a polymerization process wherein the at least one olefin monomer is propylene and the diluent is propane. In this case, it preferred that the separation step follows step (f), thus yielding a purified hydrocarbon stream comprising preferably at least 60 wt %, more preferably at least 70 wt % or 80 wt %, even more preferably at least 90 wt % or 95 wt %, still even more preferably at least 97 wt % and most preferably at least 99 wt % of propane, with wt % relative to the total weight of said purified hydrocarbon stream. The remainder of said purified hydrocarbon stream may be other hydrocarbons as defined above.

Figure 2:
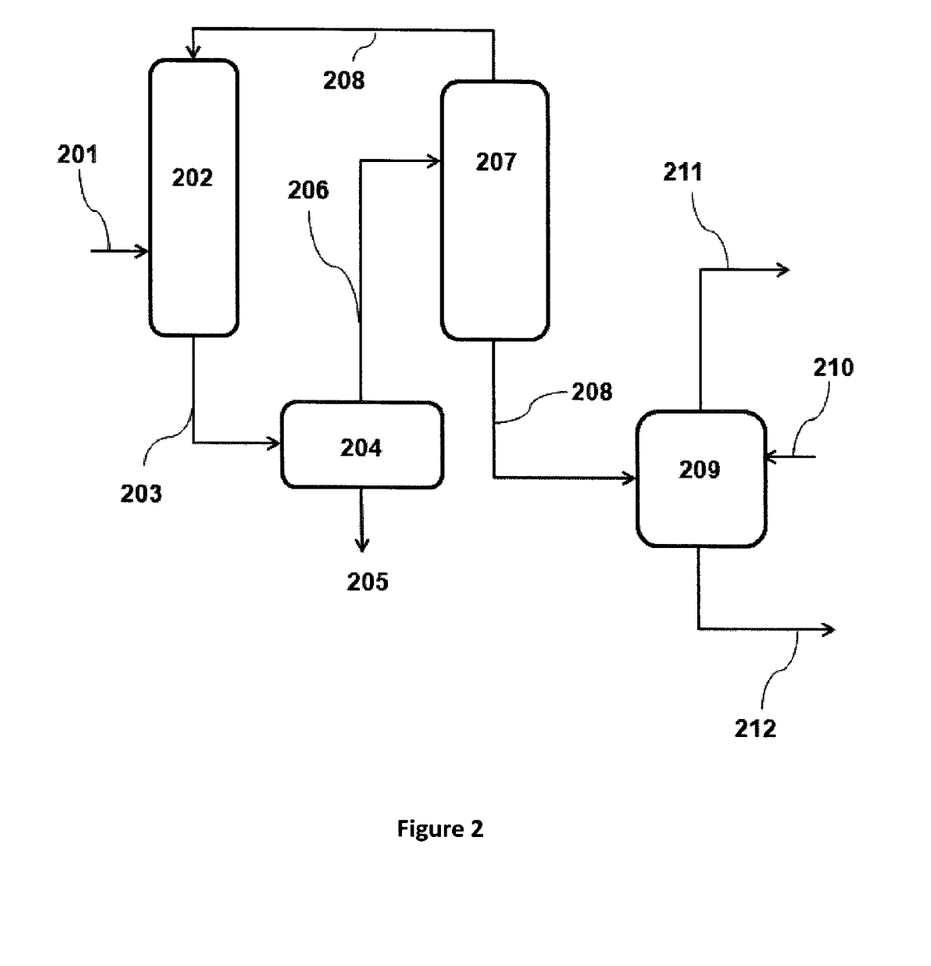
FIG. 2 shows a non-limiting exemplary schematic representation of the present process for the purification of a contaminated hydrocarbon stream as part of an olefin polymerization plant.

FIG. 2 shows a non-limiting exemplary schematic representation of a process for the purification of a contaminated hydrocarbon stream, which originates from an olefin polymerization process, particularly for an ethylene or propylene homo- or copolymerization process. The at least one olefin monomer, polymerization catalyst, co-catalyst, optional hydrogen and optional diluent are fed through one or more inlets (201) to the polymerization reactor (202), wherein polymer is formed. An effluent (203), which comprises polymer solids, one or more organoaluminum compounds, the at least one olefin monomer and—if present—the diluent, is withdrawn from the polymerization reactor (202). Subsequently, said effluent is introduced into a polymer separation zone (204), from which the polymer (205) is recovered as solids, while a contaminated hydrocarbon stream (206) comprising the lighter components of the effluent, such as unreacted olefin monomer, the one or more organoaluminum compounds and the optional diluent, is recovered as gas.

Optionally and not shown, the contaminated hydrocarbon stream (206) may further be separated into its components, for example in a splitter (207), which separates lighter from heavier components. Generally the heavier components comprise at least a part of the one or more organoaluminum compounds. For example in the slurry polymerization of ethylene, unreacted ethylene may be separated from the diluent, such as for example iso-butane, with the diluent then comprising a part of the one or more organoaluminum compounds.

In accordance with the present process the heavier ("bottom") fraction (208) from the splitter is sent as contaminated hydrocarbon stream to the contact vessel (209), in which said contaminated hydrocarbon stream (208) and a flow (210) of chemical agent capable of reacting with organoaluminum compounds are introduced, thus resulting in a purified hydrocarbon stream (211) and a stream (212) of reaction product of one or more organoaluminum compounds and the chemical agent, both of which may then removed from the contact vessel (209).

The present process for producing a purified hydrocarbon stream may for example also be used subsequent to a process for the polymerization of propylene or the copolymerization of propylene and one of more further olefins different from propylene or the copolymerization of propylene and ethylene in presence of a polymerization catalyst, one or more organoaluminum compounds and propane as diluent in a polymerization zone to produce a polypropylene. An effluent comprising polypropylene solids, propylene and propane is withdrawn from the polymerization zone. Subsequently, said effluent is introduced into a polymer separation zone, from which the polypropylene is recovered as a solid, and a contaminated hydrocarbon stream comprising propylene, propane and one or more organoaluminum compounds is recovered as gas. The contaminated hydrocarbon stream may then be introduced into a distillation zone, the distillation therein yielding a stream of propylene and a contaminated propane stream comprising one or more organoaluminum compounds and a minor amount of propylene. Said contaminated propane stream is then treated in accordance with the present process to yield a purified propane stream, which still comprises a minor amount of propylene. The so-obtained purified propane stream may then be used for example as fuel gas, co-cracking gas or LPG (liquefied petroleum gas).

With respect to the polymer separation zone, the effluent withdrawn from the polymerization zone may be treated by flashing, cooling/condensation, distillation absorption or any combination of these, depending upon the physical state of the effluent as well as the composition of the effluent. Physical phase separation of powder or particles from gas streams or liquid streams can be carried out in simple gravity separators, cyclones or any other convenient type. Such techniques are well known to the person skilled in the art and need not be described in detail.

As representative non-limiting example a liquid effluent may be passed through one or more flashing steps. Typically flashing is performed in a flash tank by letting down the pressure, thereby achieving essentially instantaneous conversion of a portion of the liquid into a gas. The gas can be drawn off from the upper part of said flash tank, while remaining liquid or solids can be retrieved from the lower part of said flash tank. As further example, a gaseous effluent may be passed through one or more cyclones to achieve separation and allow recovery of the polymer produced.

With respect to the distillation zone, commonly also referred to as "splitter", such zone may comprise one or more distillation steps. Such splitter is well known to the skilled person and need not be described in detail. In case of the (co)polymerization of propylene the stream fed to the splitter comprises for example up to about 40 wt % of propane, with the remainder comprising essentially propylene, but also lighter hydrocarbons, such as for example ethylene, as well as a small amount of heavier hydrocarbons.

The present application also discloses a chemical manufacturing plant comprising a contact vessel as defined above, wherein a contaminated hydrocarbon stream as defined above is contacted with a chemical agent as defined above. Said chemical manufacturing plant preferably further comprises at least one component of the group consisting of a storage tank for said chemical agent, a polymerization zone, a polymer separation zone and a distillation zone. More preferably said chemical manufacturing plant comprises the following components: (1) a polymerization zone, (2) a polymer separation zone, and (3) a contact vessel, wherein components (1), (2) and (3) are serially connected in this order with means to transfer liquids or solids from the preceding component to the subsequent component. Most preferably, said chemical manufacturing plant comprises the following components: (1) a polymerization zone, (2) a polymer separation zone, (3) a contact vessel, and (4) a distillation zone wherein the components are serially connected either in order (1), (2), (3) and (4) or in order (1), (2), (4), (3) with means to transfer liquids or solids from the preceding component to the subsequent component.

It has come as an unexpected benefit that the present process also allows far greater flexibility in running a chemical manufacturing site which comprises a number of different polymerization plants. Taking the example of a contaminated hydrocarbon stream originating from a copolymerization of ethylene and hexene in iso-butane using a Ziegler-Natta polymerization catalyst, a part of the one or more organoaluminum compounds will end up in the recovered hexene-fraction. If this hexene-fraction is then fed to a polymerization using a chromium-based polymerization catalyst, a significant loss in polymerization activity will be observed. Thus, the present process is particularly advantageous as it allows to re-use the recovered hexene throughout a manufacturing site without risk of negative influences, i.e. the recovered hexene can be used in the same way as fresh hexene, i.e. hexene that has not yet passed through a polymerization plant.

Test Methods

The aluminum content of a hydrocarbon stream can be determined by coupled plasma technique with atomic emission spectroscopy using an Optima 7300 DV ICP-OES spectrometer supplied by Perkin Elmer at a wavelength of 308.2 nm. Samples were injected directly without any previous preparation. If necessary the sample may be diluted.

Examples

The present purification process was tested in an industrial propylene polymerization plant for a duration of ca. 2 months.

In a stirred tank reactor propylene was polymerized in a polymerization medium comprising propylene, propane, a Ziegler-Natta polymerization catalyst, triethyl aluminum (TEAL), hydrogen and polypropylene solids. An effluent comprising polypropylene solids (including the polymerization catalyst residues), propylene, propane, hydrogen and TEAL were continuously withdrawn from the reactor.

The effluent was then fed to a polymer separation zone, wherein the polypropylene solids were separated from a contaminated hydrocarbon stream consisting of the remainder of the effluent comprising propylene, propane and TEAL with a propylene to propane weight ratio of 9.

In a subsequent distillation zone (splitter), the propylene was mostly eliminated from the contaminated hydrocarbon stream, which after the distillation zone comprised ca. 3 wt % of propylene, ca. 97 wt % of propane, and on average ca. 20 ppm by weight of aluminum (corresponding to ca. 75 ppm by weight of TEAL), relative to the total weight of said contaminated hydrocarbon stream.

The contaminated hydrocarbon stream was fed at a rate of about 0.77 t/h and a temperature of about 65° C. to the lower end of the contact vessel of the shower tray type. From the upper end of the contact vessel a solution of 200 l Atmer 168 ($C_{14/16}N(CH_2—CH_2—OH)_2$, CAS-number 71786-60-2) in 400 l mineral oil was run counter-currently to the contaminated hydrocarbon stream, thus allowing the TEAL and the Atmer 168 to react.

A purified hydrocarbon stream was recovered as overhead near the upper end of the contact vessel. From the lower end of the contact vessel a solution comprising mineral oil, unreacted Atmer 168 and the reaction production between Atmer 168 and TEAL was recovered.

Aluminum content of the purified hydrocarbon stream was checked by spot measurements, the results of which are indicated in Table I.

TABLE I

| Total amount of contaminated hydrocarbon stream treated [t] | Aluminum content of purified hydrocarbon stream [ppm by weight] |
|---|---|
| 125 | 0.020 |
| 300 | 0.035 |
| 560 | 0.030 |
| 1000 | 0.015 |

These results clearly show the efficiency of the present purification process. It was under industrial conditions at all times possible to keep the aluminum content of the purified hydrocarbon stream well below 0.05 ppm, relative to the total weight of the purified hydrocarbon stream.

The present test run was performed using a discontinuous removal of the solution of Atmer 168 and the reaction product of Atmer 168 and TEAL. With a solution originally containing 200 l of Atmer 168 it was possible to treat a total of more than 1000 t of contaminated hydrocarbon stream (essentially consisting of propane) before said solution reached a concentration of ca. 15 wt % of TEAL.

Figure 3:
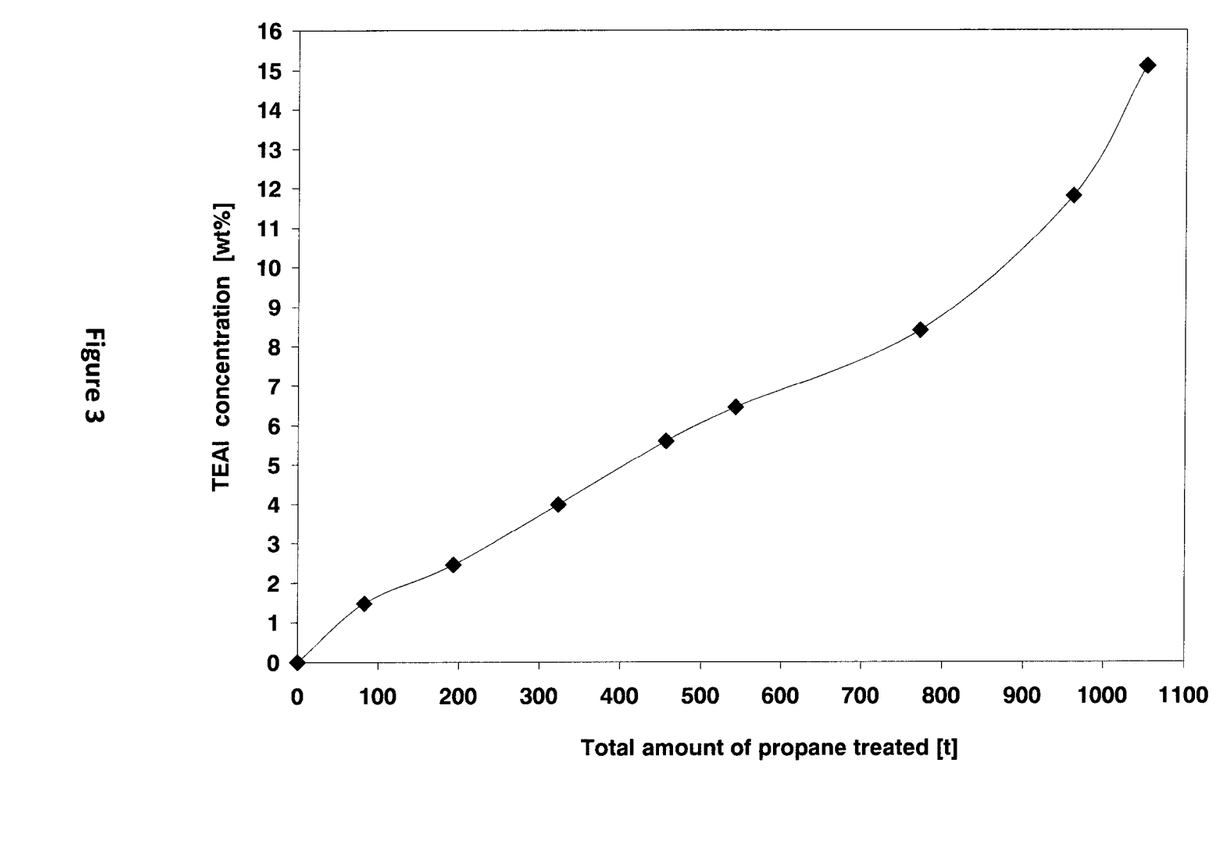
FIG. 3 is a graph showing the increase in the concentration of TEAL, given as wt % relative to the total weight of the solution, in the solution of Atmer 168 over the course of a test run, wherein a contaminated propane stream comprising TEAL was purified.

FIG. 3 is a graph showing the increase in the concentration of TEAL, given as wt % relative to the total weight of the solution, in the solution of Atmer 168 over the course of the test run.

The recovered purified propane could be sold as liquefied petroleum gas and thus did not have to be disposed of at high financial as well as environmental cost, e.g. by flaring off.

While this example shows the efficiency and advantages of the present process in an industrial propylene polymerization plant it is clear to the skilled person that it can easily be adapted to be used in other chemical manufacturing processes.

The invention claimed is:

1. A process comprising:
   (i) contacting in a contact vessel a contaminated hydrocarbon stream and a chemical agent, wherein the contaminated hydrocarbon stream comprises one or more organoaluminum compounds, thereby producing a purified hydrocarbon stream, wherein the purified hydrocarbon stream has an aluminum content lower than an aluminum content of the contaminated hydrocarbon stream; and
   (ii) withdrawing said purified hydrocarbon stream from said contact vessel;
   wherein the chemical agent is selected from a group consisting of $H-X^1$, $X^1-A^1-X^2$, $X^1-A^1-A^2-X^2$ and $X^1-A^3=A^4-X^2$, wherein:
   $A^1$ and $A^2$ are independently selected from a group consisting of $CR^1R^2$, $C=O$ and $NR^1$;
   $A^3$ and $A^4$ are either independently selected from a group consisting of $CR^1$ and N or alternatively both, $A^3$ and $A^4$, are a carbon forming part of an aromatic ring or fused ring system;
   $X^1$ and $X^2$ are independently selected from a group consisting of $OR^1$, $SR^1$, $=NR^1$, $NR^1R^2$, $PR^1R^2$, $C(=O)R^1$, $C(=O)OR^1$, $OC(=O)R^1$, $C(=O)NR^1R^2$ and $NR^1C(=O)R^2$; and
   $R^1$ and $R^2$ are independently selected from a group consisting of hydrogen, alkyl, aryl, substituted alkyl and substituted aryl, wherein substituted alkyl denotes an alkyl substituted with $X^1$ and substituted aryl denotes an aryl substituted with $X^1$;
   with the provision that $H-X^1$ is not HOH;
   wherein the chemical agent is dissolved or suspended in a liquid saturated hydrocarbon.

2. The process of claim 1, wherein $A^1$ and $A^2$ are independently selected from $CR^1R^2$ and $C=O$.

3. The process of claim 1, wherein $A^1$ and $A^2$ are $CR^1R^2$.

4. The process of claim 1, wherein $A^3$ and $A^4$ are $CR^1$.

5. The process of claim 1, wherein $A^3$ and $A^4$ are a carbon forming part of an aromatic ring or fused ring system.

6. The process of claim 1, wherein $X^1$ and $X^2$ are independently selected from $OR^1$, $=NR^1$, $NR^1R^2$, $C(=O)OR^1$ and $C(=O)NR^1R^2$.

7. A process comprising:
   (i) contacting in a contact vessel a contaminated hydrocarbon stream and a chemical agent, wherein the contaminated hydrocarbon stream comprises one or more organoaluminum compounds, thereby producing a purified hydrocarbon stream, wherein the purified hydrocarbon stream has an aluminum content lower than an aluminum content of the contaminated hydrocarbon stream; and
   (ii) withdrawing said purified hydrocarbon stream from said contact vessel;
   wherein the chemical agent is selected from a group consisting of $H-X^1$, $X^1-A^1-X^2$, $X^1-A^1-A^2-X^2$ and $X^1-A^3=A^4-X^2$, wherein:
   $A^1$ and $A^2$ are independently selected from a group consisting of $CR^1R^2$, $C=O$ and $NR^1$;
   $A^3$ and $A^4$ are either independently selected from a group consisting of $CR^1$ and N or alternatively both, $A^3$ and $A^4$, are a carbon forming part of an aromatic ring or fused ring system;
   $X^1$ and $X^2$ are independently selected from a group consisting of $OR^1$, $SR^1$, $=NR^1$, $NR^1R^2$, $PR^1R^2$, $C(=O)R^1$, $C(=O)OR^1$, $OC(=O)R^1$, $C(=O)NR^1R^2$ and $NR^1C(=O)R^2$; and
   $R^1$ and $R^2$ are independently selected from a group consisting of hydrogen, alkyl, aryl, substituted alkyl and substituted aryl, wherein substituted alkyl denotes an alkyl substituted with $X^1$ and substituted aryl denotes an aryl substituted with $X^1$;
   with the provision that $H-X^1$ is not HOH;
   wherein a temperature in the contact vessel is above a boiling point of the contaminated hydrocarbon stream.

8. The process of claim 7, wherein the chemical agent is not dissolved or suspended in a liquid.

9. The process of claim 7, wherein the chemical agent is $HO-CH_2-CH_2-O-(CH_2-CH_2-O)_m-H$, wherein m is from 0 to 400 or is an ethoxylated alkylamine of formula $(C_pH_{2p+1})_qN(CH_2-CH_2-OH)_{3-q}$ with p being in the range from 1 to 30 and q being 0, 1 or 2.

10. The process of claim 7, wherein the one or more organoaluminum compounds are selected from a group consisting of: organoaluminum compounds represented by the following general formula $R_{3-n}AlX_n$ (I), wherein each R is independently selected from alkyl having from one to ten carbon atoms, each X is independently a halogen atom, and n is 0, 1 or 2; alkylalumoxanes wherein alkyl is selected from alkyl having from one to ten carbon atoms; and blends thereof.

11. The process of claim 7, wherein the organoaluminum compound is triethylaluminum or methylalumoxane.

12. The process of claim 7, wherein the purified hydrocarbon stream has an aluminum content of at most 60 wt % of the aluminum content of the contaminated hydrocarbon stream, wherein the aluminum content is determined by coupled plasma technique with atomic emission spectroscopy.

13. A process comprising:
   (i) contacting in a contact vessel a contaminated hydrocarbon stream and a chemical agent, wherein the contaminated hydrocarbon stream comprises one or more organoaluminum compounds, thereby producing a purified hydrocarbon stream, wherein the purified hydrocarbon stream has an aluminum content lower than an aluminum content of the contaminated hydrocarbon stream; and
   (ii) withdrawing said purified hydrocarbon stream from said contact vessel;
   wherein the chemical agent is an ethoxylated amine of formula $(C_pH_{2p+1})N(CH_2-CH_2-OH)_2$, wherein p is from 12 to 18.

14. A process comprising:
obtaining a contaminated hydrocarbon stream by:
   (a) polymerizing at least one olefin monomer in a polymerization zone in a polymerization medium to produce a polymer, said polymerization medium comprising polymer solids, one or more organoaluminum compounds and the at least one olefin monomer;

(b) withdrawing from said polymerization zone an effluent comprising the polymer solids, the one or more organoaluminum compounds and the at least one olefin monomer;
(c) separating from said effluent the contaminated hydrocarbon stream comprising the at least one olefin monomer and the one or more organoaluminum compounds;
(i) contacting in a contact vessel the contaminated hydrocarbon stream and a chemical agent, wherein the contaminated hydrocarbon stream comprises one or more organoaluminum compounds, thereby producing a purified hydrocarbon stream, wherein the purified hydrocarbon stream has an aluminum content lower than an aluminum content of the contaminated hydrocarbon stream; and
(ii) withdrawing said purified hydrocarbon stream from said contact vessel;
wherein the chemical agent is selected from a group consisting of $H-X^1$, $X^1-A^1-X^2$, $X^1-A^1-A^2-X^2$ and $X^1-A^3=A^4-X^2$, wherein:
$A^1$ and $A^2$ are independently selected from a group consisting of $CR^1R^2$, $C=O$ and $NR^1$;
$A^3$ and $A^4$ are either independently selected from a group consisting of $CR^1$ and N or alternatively both, $A^3$ and $A^4$, are a carbon forming part of an aromatic ring or fused ring system;
$X^1$ and $X^2$ are independently selected from a group consisting of $OR^1$, $SR^1$, $=NR^1$, $NR^1R^2$, $PR^1R^2$, $C(=O)R^1$, $C(=O)OR^1$, $OC(=O)R^1$, $C(=O)NR^1R^2$ and $NR^1C(=O)R^2$; and
$R^1$ and $R^2$ are independently selected from a group consisting of hydrogen, alkyl, aryl, substituted alkyl and substituted aryl, wherein substituted alkyl denotes an alkyl substituted with $X^1$ and substituted aryl denotes an aryl substituted with $X^1$;
with the provision that $H-X^1$ is not HOH.

15. The process of claim 14, wherein the polymerization medium, the effluent, the contaminated hydrocarbon stream, and the purified hydrocarbon stream comprise a diluent.

16. The process of claim 14, wherein the at least one olefin monomer is ethylene or propylene.

17. The process of claim 14, further comprising, subsequently to step (c):
(c') separating the at least one olefin monomer from the contaminated hydrocarbon stream of (c) prior to feeding the contaminated hydrocarbon stream to the contacting vessel.

18. The process of claim 14, further comprising, subsequently to withdrawing the purified hydrocarbon stream from the contact vessel, separating the at least one olefin monomer from the purified hydrocarbon stream.

* * * * *